United States Patent
Heck et al.

(10) Patent No.: US 7,123,137 B2
(45) Date of Patent: Oct. 17, 2006

(54) PATIENT SAFETY AND ALERTING SYSTEM

(75) Inventors: David Alan Heck, Zionsville, IN (US); Kathryn Gardner Rapala, Carmel, IN (US); Philip H. Canada, Fishers, IN (US)

(73) Assignee: Clarian Health Partners, Inc., Indianapolis, IN (US)

( * ) Notice: Subject to any disclaimer, the term of this patent is extended or adjusted under 35 U.S.C. 154(b) by 102 days.

(21) Appl. No.: 10/878,829

(22) Filed: Jun. 28, 2004

(65) Prior Publication Data

US 2005/0285745 A1 Dec. 29, 2005

(51) Int. Cl.
*G08B 29/00* (2006.01)

(52) U.S. Cl. .................. 340/506; 340/507; 340/573.1; 705/3; 128/845

(58) Field of Classification Search ............. 340/573.1, 340/506, 507; 128/845, 870, 653.1, 653.2; 705/2, 3; 715/783
See application file for complete search history.

(56) References Cited

U.S. PATENT DOCUMENTS

| | | | |
|---|---|---|---|
| 5,267,147 A | 11/1993 | Harshaw et al. | |
| 5,319,355 A | 6/1994 | Russek | |
| 5,416,695 A | 5/1995 | Stutman et al. | |
| 5,452,416 A * | 9/1995 | Hilton et al. | 715/783 |
| 5,534,851 A | 7/1996 | Russek | |
| 5,553,618 A * | 9/1996 | Suzuki et al. | 600/411 |
| 5,579,775 A | 12/1996 | Dempsey et al. | |
| 5,924,074 A | 7/1999 | Evans | |
| 6,032,035 A | 2/2000 | Webster et al. | |
| 6,085,752 A | 7/2000 | Kehr et al. | |
| 6,230,142 B1 * | 5/2001 | Benigno et al. | 705/3 |
| 6,347,329 B1 | 2/2002 | Evans | |
| 6,401,072 B1 * | 6/2002 | Haudenschild et al. | 705/3 |
| 6,445,304 B1 | 9/2002 | Bandeian, Jr. et al. | |
| 6,488,029 B1 * | 12/2002 | Hood et al. | 128/845 |
| 6,607,481 B1 | 8/2003 | Clawson | |

(Continued)

FOREIGN PATENT DOCUMENTS

WO WO 94/22098 9/1994

(Continued)

OTHER PUBLICATIONS www.siemensmedical.com/webapp/wcs/stores/servlet/PressReleaseView?langId=1 . . . Oct. 22, 2003.

(Continued)

*Primary Examiner*—Van T. Trieu
(74) *Attorney, Agent, or Firm*—Ice Miller LLP; Homer W. Faucett, III; Doreen J. Gridley

(57) ABSTRACT

A patient safety alerting system and methods for providing enhanced patient safety using a patient alerting system are provided. An illustrative patient safety alerting system comprises an output device comprising a set of indicators, each indicator displaying one of a plurality of indicator states, each of the indicator states indicating a level of compliance with patient safety procedures; a set of status lists, each status list corresponding to its respective indicator, wherein the displayed indicator state of the respective indicator corresponds to information in the respective status list, each status list provided for containing information regarding the status of a patient for a component or activity; a processing unit operatively connected to the output device for processing changes to the status lists and corresponding indicators; and an input device operatively connected to the processing unit and configured to interface with a user to allow the user to access information in any of the status lists.

24 Claims, 4 Drawing Sheets

U.S. PATENT DOCUMENTS

| | | |
|---|---|---|
| 2002/0016719 A1 | 2/2002 | Nemeth et al. |
| 2002/0046346 A1 | 4/2002 | Evans |
| 2002/0082480 A1 | 6/2002 | Riff et al. |
| 2002/0120310 A1 | 8/2002 | Linden et al. |
| 2003/0074222 A1 | 4/2003 | Rosow et al. |
| 2003/0204411 A1 | 10/2003 | Beyersdorf |

FOREIGN PATENT DOCUMENTS

| | | |
|---|---|---|
| WO | WO 02/41761 A 2 | 5/2002 |
| WO | WO 03/091823 A 2 | 11/2003 |

OTHER PUBLICATIONS www.siemensmedical.com/webapp/wcs/stores/servlet/CategoryDisplay?categoryId . . . Oct. 22, 2003.
www.siemensmedical.com/webapp/wcs/stores/servlet/CategoryDisplay?storeId=10 . . . Oct. 22, 2003.
www.bridgemedical.com/patient_safety.shtml Oct. 22, 2003.
www.cpsinet.com/system/moduleindex.htm Oct. 22, 2003.

* cited by examiner

PATIENT SAFETY AND ALERTING SYSTEM

FIELD OF THE INVENTION

This invention relates to alerting systems, illustratively alerting systems for patient safety.

BACKGROUND OF THE INVENTION

Alerting systems have been used as part of safety practices in various industries. For example, in the 1930s, submarines were introduced with a novel alerting system. Historically, accidents occurred when major openings through the pressure hull had not been closed prior to diving. These apparently obvious errors had resulted in the loss of boats and lives. To improve communication about the status of the submarine, an alerting system was developed. This system incorporated visual feedback to the dive officer and the captain about the status of all openings to the sea. When a particular hull opening was not closed to the sea, the corresponding indicator would be set to a "Red" colored state. When this hull opening was closed, the indicator would be set to a "Green" state. The submarine personnel could quickly glance at the state of the "Greenboard" or "Christmas Tree" prior to giving the order to dive. This safety system is believed to have reduced the likelihood of loss of submarines in the United States Navy.

In aviation, similar safety systems have been implemented. Some of the more advanced aviation systems have incorporated electronic checklists with visual and auditory alerting. Other industries in which operational safety is paramount, including the nuclear power industry and in the launching of nuclear missiles, have incorporated similar alerting systems.

The Agency for Health Care Research and Quality (AHRQ) has proposed that medical institutions introduce safety practices similar to those used in other industries. An analysis of "sentinel events," events involving death or serious injury, has found that the Operating Room (OR) has the highest incidence of patient safety "events." Examples of OR events that represent potential opportunities for improvement include anything that does or could cause patient harm. Examples of events that do or could contribute to patient harm include: wrong site surgical procedures, not providing needed medications, incorrect timing of medications, incomplete instrumentation, incorrect instrumentation, lack of needed supplies, incorrect supplies, lack of medical records, lack of relevant imaging, sponge counting, needle counting, and others.

Additionally, the Joint Commission on Accreditation of Healthcare Organizations (JCAHO) has begun to survey all JCAHO accredited health care organizations for implementation of the following recommendations—or acceptable alternatives—as appropriate to the services the organization provides. Failure by an organization to implement any of the applicable recommendations (or an acceptable alternative) will result in a special Type I recommendation. The specific goals of this initiative include:

1. Improve the process of patient, surgical site and procedure verification.
   a. Extend the current preoperative verification process by implementing an electronic checklist.
   b. Facilitate this identification and comply with 2003 JCAHO criteria by confirming and recording that appropriate documents (e.g., medical records, imaging studies) are available at the time of the surgical episode.
   c. Implement a process to mark the surgical site and involve the patient in the marking process.
2. Improve the effectiveness of communication among caregivers in the delivery of surgical care.
3. Improve the timely administration of prophylactic antibiotics.
4. Improve the effectiveness of clinical alerting systems.
5. Provide a closed loop feedback system to support ongoing process improvement.

Presently, most procedures that are implemented to reduce "sentinel events" comprise manual checklists. Not only is the use of such lists cumbersome, manual checklists are prone to error by the person completing the checklist. Also, if a step is omitted, it is often difficult to determine if the step had actually been omitted, or if the person performing the step merely failed to fill out the form. This is particularly problematic if the oversight is not noted immediately. The automated checklist in U.S. Pat. No. 5,267,147 overcomes some of these shortcomings, but relies on sequential review of checklist items.

Medical alert or alarm systems for equipment operation or patient conditions are also known. U.S. Pat. Nos. 5,319,355 and 5,534,851 provide an alarm for a life support system that provides information for "medical conditions of patients and the status and operational conditions of any medical equipment that may be used in a pre-hospital, post-hospital, or in-hospital setting." Col. 3, lines 29–32 (See also Col. 4, lines 7–22). U.S. Pat. No. 5,416,695 discloses a medical alert system used for medical and geodetic information, such as for use with ambulatory patients. U.S. Pat. No. 5,579,775 teaches a telemetry system for monitoring a patient's physiological conditions. U.S. Pat. No. 6,032,035, discloses a portable transmitter for an emergency response system, and U.S. Pat. No. 6,607,481, discloses an emergency call system for dispatchers. U.S. Publication Nos. 2002/0082480 and 2002/0120310, disclose systems for management of medical devices. U.S. Publication 2003/0022815 displays tasks for patient care, and PCT Publication No. WO 94/22098 discloses a patient care and communication system. While many of these alert systems and automated checklists, the references for which are herein incorporated by reference, could be used in connection with the present invention, none of these systems teaches a display of the status of various safety activities applicable to a particular healthcare environment.

It is desired to provide an alert system for patient care, illustratively for use in various healthcare environments, such as the operating room, that easily alerts appropriate medical personnel of any deficiencies, including missing information, tests, or materials required for surgery. Such a system would operate to minimize events that do or could cause harm to the patient. Illustratively, the system would provide appropriate alerts in pre-operative, operative, and post-operative environments. However, it is understood that the systems and methods may be used for other aspects of patient care.

SUMMARY OF THE INVENTION

The present invention comprises alerting systems and methods for improving patient safety. Illustratively, a patient safety alerting system is provided comprising an output device, illustratively a computer screen, showing a set of indicators, each indicator displaying one of a plurality of indicator states, illustratively a green circle, a yellow triangle, and a red octagon. The system also comprises a set of status lists, each status list corresponding to its respective indicator, wherein the displayed indicator state of the respective indicator corresponds to information in the respective status list. The alerting system also comprises a processing unit operatively connected to the output device for processing changes to the status lists and corresponding indicators and an input device operatively connected to the processing unit and configured to interface with a user to allow the user to view and update information in the status lists. Optionally, the processing unit may be operatively connected to one or more other systems and may receive information needed for various status lists from these other systems. Illustratively, the set of indicators are for a specific hospital environment, and the entire set of indicators is displayed on a single computer screen, although various indicators could be displayed on multiple displays. Other sets of indicators for other hospital environments may be provided and displayed on other screens.

In one particular embodiment, Pre-Operative, Operative, and Post-Operative comprise three hospital environments, each comprising a set of status lists and a corresponding set of indicators. Illustratively, all indicators of one of the environments are visible at one time, and the user can page between screens for each of the environments.

Because all of the indicators for an environment are displayed on a single screen, the user can readily assess the patient status with respect to that environment. The user can also access any of the status lists in any order, particularly ones for which the indicator shows a non-compliant indicator state. The user can update information contained in the status lists, as is appropriate, and, in the illustrated embodiment, the user can move to a different screen to show all indicators in another environment.

Additional features of the present invention will become apparent to those skilled in the art upon consideration of the following detailed description of preferred embodiments exemplifying the best mode of carrying out the invention as presently perceived.

DETAILED DESCRIPTIONS OF ILLUSTRATIVE EMBODIMENTS

Figure 1:
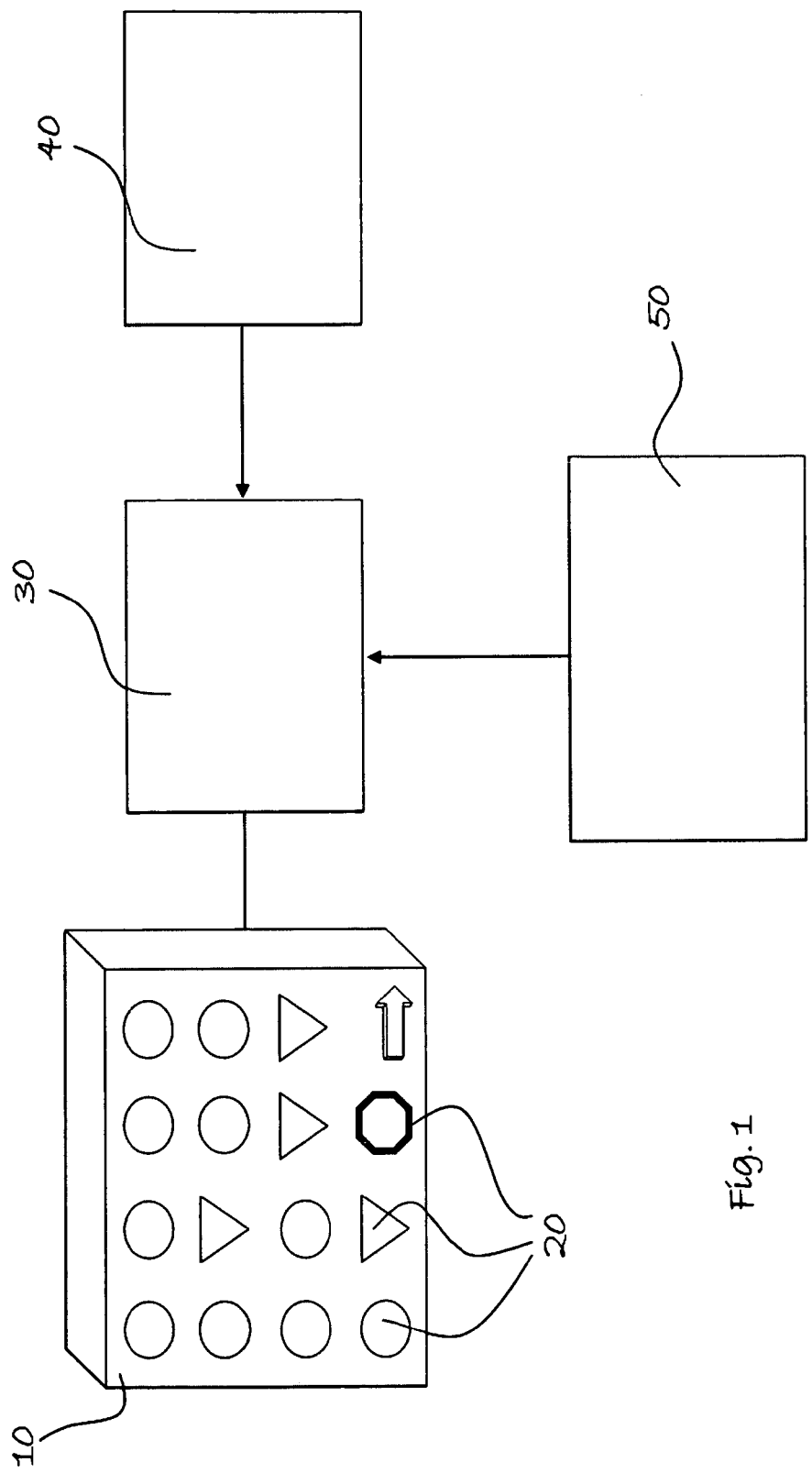
FIG. 1 is a diagrammatic representation showing the input and output of information from an alerting system.

The present invention comprises a system and method for providing comprehensive alerting related to patient safety in various healthcare environments. FIG. 1 provides an overview of a patient alerting system according to this disclosure. An output device, for example the computer screen 10, displays a set of indicators 20 for a particular patient environment, each indicator displaying the status of a component or activity necessary for that environment. Illustratively, with a single view of the screen, the user can quickly assess the status of the patient with respect to that environment. The status of each indicator is maintained by processing unit 30. Information may be provided to the processing unit 30 from one or more outside systems 40 (e.g. imaging, medical records, etc.), or may be provided by the user through a user interface 50, illustratively a touch screen, keyboard, mouse, or other input device, as is known in the art. Outside systems 40 are operationally connected to processing unit 30 by means well known in the art, such as networks or direct communications, to permit retrieval of data from outside systems 40 by processing unit 30 for display on computer screen 10.

In one illustrative embodiment, the system comprises three phases that parallel the existing list process sequencing for three different hospital or healthcare environments. The clustering of activities for each of these environments minimizes excessive alerting to staff when not directly applicable to their present job activities. In the present example, the phases include:

Pre-operative
Operative
Initial Post-Operative

Figure 2:
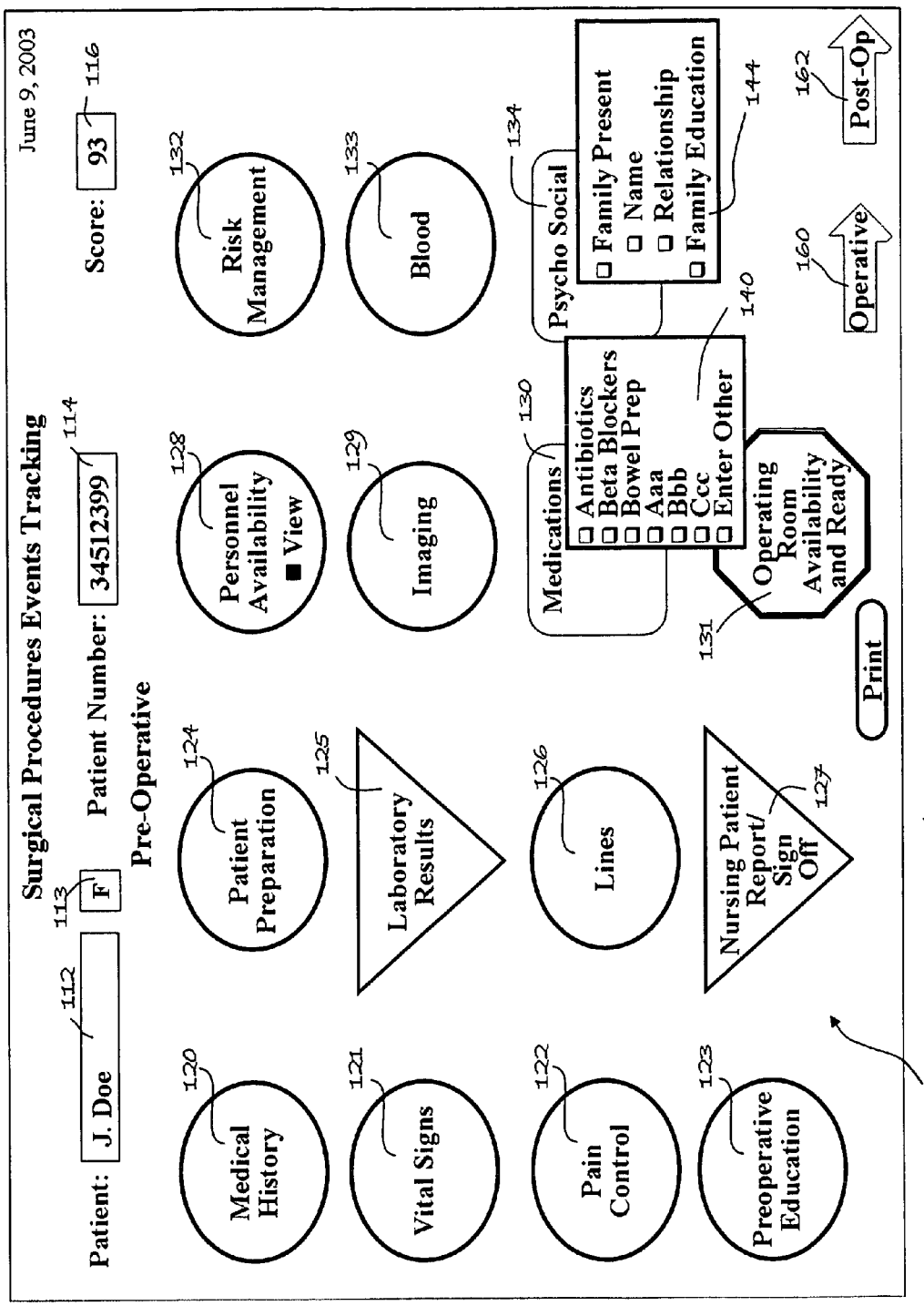
FIG. 2 is a Pre-Operative screen showing a first set of indicators and several status lists.
Figure 3:
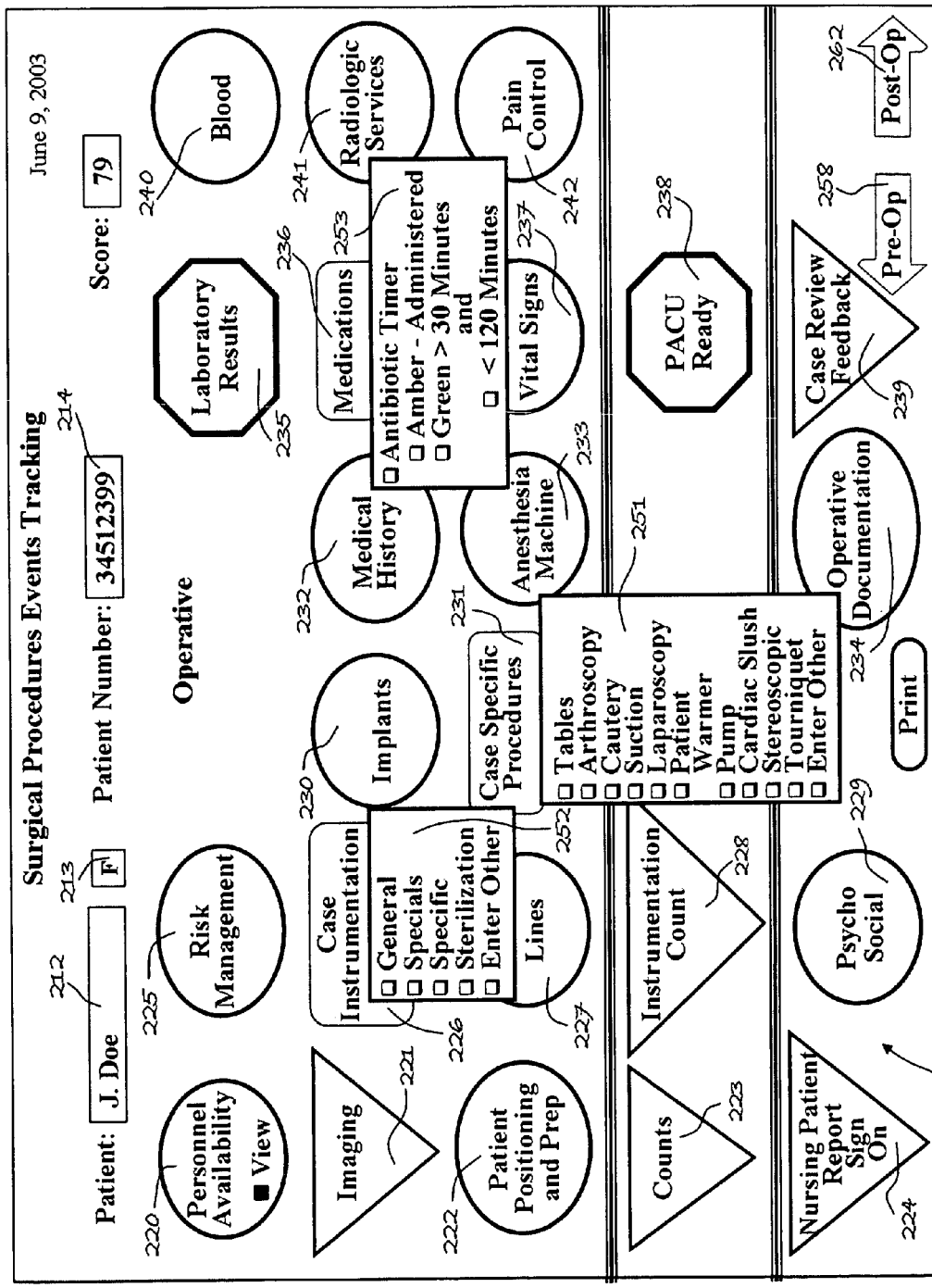
FIG. 3 is an Operative screen showing a second set of indicators and several status lists.
Figure 4:
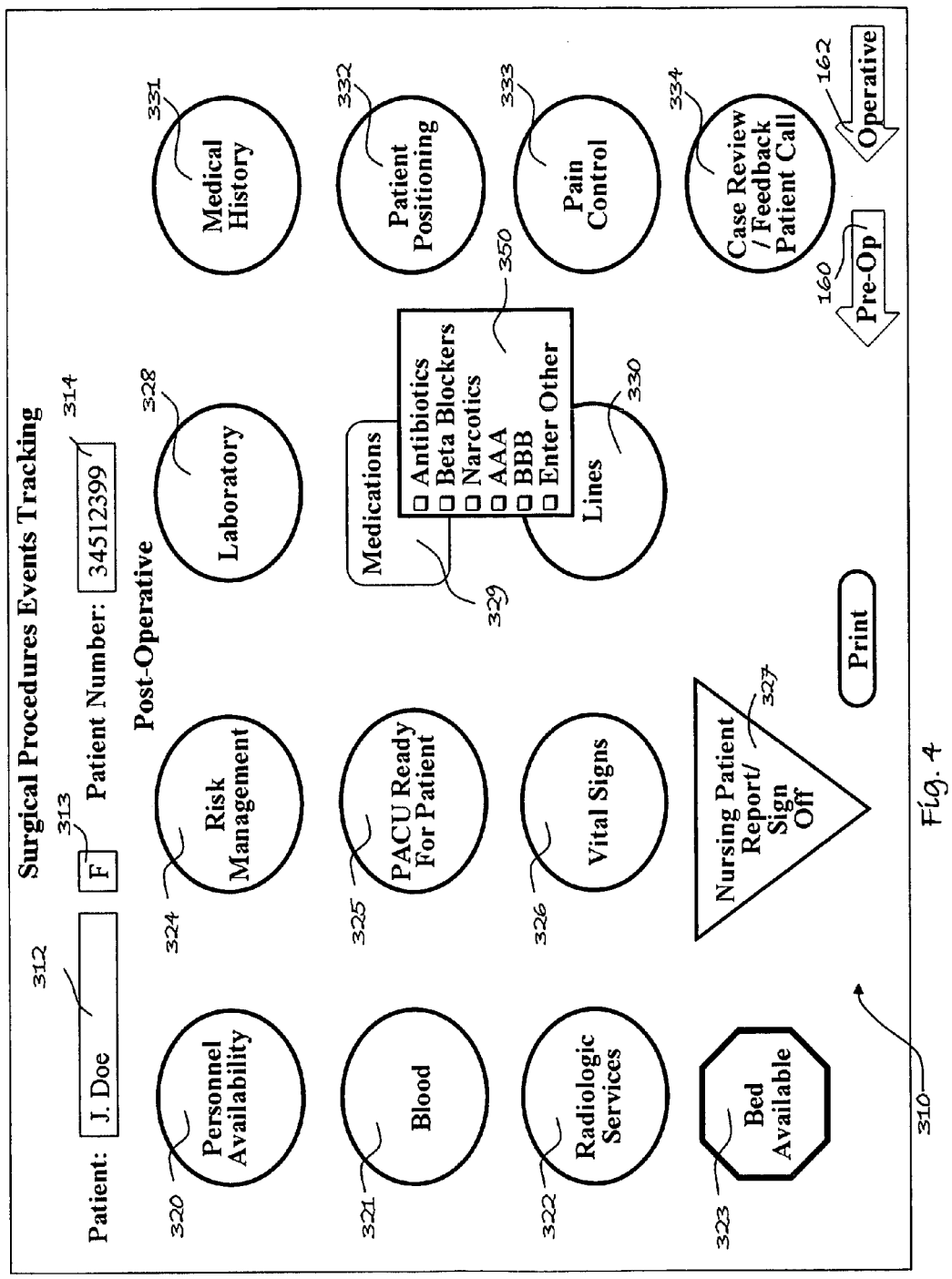
FIG. 4 is a Post-Operative screen showing a third set of indicators and several status lists.

FIGS. 2–4 show exemplary computer screens for the Pre-Operative 110, Operative 210, and Initial Post-Operative 310 environments, respectively. These screens may be displayed on custom hardware or may be displayed on hardware readily available to medical personnel involved in the applicable environment. Illustratively, such hardware is operatively connected to other systems 40 used the healthcare provider, to obtain information, images, and the like, as is stored on such systems 40.

At each "phase" or "environment" of the surgical episode, the system as illustrated in FIGS. 2–4 provides series of items or "status lists" that are safety components or activities for the phase. As provided in the illustrated embodiment, each of the three phases have unique components, but the three phases also comprise common components or activities that may be required at each demarcation. Because the status of all components for a particular environment is displayed together in an easily discernable manner, the system is more than a checklist. The display serves as an alerting system, allowing users to quickly cross check that all safety conditions and inputs are met before commencing the next medical procedure. Many of the indicators displayed on the screen (also known as an "indicator board" or "dashboard") are determined and driven by corresponding status lists. When an indicator shows a status other than one indicating compliance, the user can check the appropriate status list to determine actions that are needed before proceeding with patient treatment. The user can move from one status list to another in any order, and the user does not need to follow a sequential list to access the status of a particular activity. Thus, the system alerts the user to non-compliant activities, and allows the user quick access to the relevant information.

The content and selection of the status lists provided in the system may be modified when necessary, as information needed for a particular environment changes, and may be modified for various other environments or phases. As shown in FIGS. 2–4, indicators 120 through 134, 220 through 242, and 320 through 334 may be arranged to prioritize tasks and to address sentinel events. The selection and arrangement of the various indicators may be modified as needed, illustratively for different procedures, different facilities, or for improvement.

For certain operating room procedures, it may be preferable to display the various indicators for each of the three "phases" or environments on its own display screen, since the safety concerns of each environment differs from that of the other environments, at least to some extent. Thus, in one embodiment, a set of Pre-Operative indicators 120 through 134 are on the Pre-Operative screen 110, a set of Operative indicators 220 through 242 are on the Operative screen 210, and a set of Initial Post-Operative indicators 320 through 334 are on the Post-Operative screen 310. Each indicator is capable of indicating various indicator states, illustratively displayed as a "stop light" or as stop light components, to allow the user at a glance to determine the readiness of each of the components or activities displayed on the screen. In the Pre-Operative screen 110 shown in FIG. 2, indicator 131, labeled "Operating Room Availability and Ready," is shown as a red stop sign, indicating that the operating room is not available or not ready. Indicators 235 and 238, labeled "Laboratory Results" and "PACU Ready," are shown as stop signs in the Operative screen 210 of FIG. 3, and indicator 323, labeled "Bed Available," is shown as a stop sign in the Post-Operative screen 310 of FIG. 4. Continuing with the stop light theme, displaying green may be used as a signal that the respective area is compliant within the guidelines, whereas non-readiness would be indicated by either yellow or red, depending on the severity of the lack of readiness. In addition to color as an indicator, a background shape may be chosen to allow those people who lack the ability to discriminate color to identify the indicator state. Illustratively, conventional symbols such as a red stop sign is used for "stop", a yellow triangle is used for "caution" and a green circle is used for "go." Indicators 125, 127, 221, 223, 228, 239, and 327 show the yellow triangle, while most of the rest of the indicators in FIGS. 2–4 show a green circle, indicating compliance for that activity. It is understood, however, that other symbols, shadings, and/or colors may be used, as is desired and appropriate for a particular application. Also, additional visual, auditory, or external alarms may be employed, which may be activated if the user attempts to go forward when the indicators show an unacceptable level of compliance, illustratively when one or more of the indicators shows the red stop sign, if too many of the indicators show the yellow caution triangle, or if the score (as discussed below) is of an unacceptable value. Visual alarms illustratively may include flashing screens, auditory alarms illustratively may include bells, buzzers, or voice feed back, and external alarms may be various other alarms found in the healthcare environment.

As illustrated in FIGS. 2–4, the user may access the status lists for each of the respective indicators. Illustratively, the user may access a list by using the input device 50 to select a desired indicator. The user may then change information shown in the list. In FIGS. 2–4, the various status lists 140, 144, 251, 252, 253, and 350 are shown as small dialog boxes adjacent to or overlapping the respective indicators. Since the status lists appear as only small dialog boxes and do not substantially obscure other information, the user can tend to the information in the various status boxes while still monitoring all of the indicators for that environment.

To further enhance the utility of the indicators, certain indicators can be provided that change their state based on time from initial activation or from a certain entry into a status list. The updating requires logic and background calculations depending upon the specifics of the alert, and such can be programmed into the system, as is known in the art. For example, for certain activities, if the information is not updated within a certain period of time, the indicator state may change from green to yellow, or from yellow to red. Updating the information would be required to change the indicator state back to green. An example is illustrated in status list 253, which would show the green circle if antibiotics were administered between 30 minutes and 120 minutes ago, but would turn to the yellow (or amber) triangle if the antibiotics were administered, but had been administered outside that time period. The system would automatically update this status based on the time of administration and the pharmokinetics of the specific antibiotic.

As shown, each screen may have additional patent information, such as patient name, 12, 212, 312, gender, 113, 213, and 313, a patient identification number 114, 214, 314, and any other relevant information. Illustratively, a score 116, 216, 316 may be used to indicate an aggregate level of compliance and the patient readiness for the next action. Optionally, the score may be expressed as an aggregate score or may be expressed as a percentage. Also, in one preferred embodiment, the screens and their respective indicators are provided such that the status of the indicators are visually noticeable from a distance of at least ten feet, and more desirable would be fifteen feet.

Optionally, some or all of the status information may be reported to a quality assurance reporting system. This reporting may be done automatically without input from the user, or the user may be prompted to submit the information during one or more of the phases.

The following is a list of possible indicators that may be used for each of the three exemplary "phases" described in the operating room embodiment. It is understood that the list is not exhaustive, and that the list may be modified, depending on the specific application.

TABLE 1

Indicators for Operating Room Alerting System

| Pre-Operative | Operative | Post-Operative |
| --- | --- | --- |
| Experimental Participant | Experimental Participant | Experimental Participant |
| Medical History Available | Medical History Available | Medical History Available |
| Medical Records Available | Medical Records Available | Medical Records Available |
| Personnel Available | Personnel Available | Personnel Available |
| Patient Site Preparation (Scrub) | Patient Site Preparation (Verification and Scrub) | Patient Positioning |
| Pain Control | Pain Control | Pain Control |
| Risk Management (Operative Consent Present, Patient ID Band, Operative Site Marked, Procedure verification) | Risk Management (Operative Consent Present, Patient ID Band, Operative Site Marked, Procedure verification) | |
| Vital Signs | Vital Signs | Vital Signs |
| Blood for Transfusion Available (when Ordered) | Blood for Transfusion Available when Ordered | Blood for Transfusion Available when Ordered |
| Laboratory Orders and Results | Laboratory | Laboratory |

TABLE 1-continued

Indicators for Operating Room Alerting System

| Pre-Operative | Operative | Post-Operative |
|---|---|---|
| Lines (IV) | Lines (IV, CVP, Arterial, Urinary Catheter, etc.) | Lines |
| Medication | Medication | Medication |
|  | Radiologic Services | Radiologic Services |
| Imaging | Imaging |  |
|  | Case Instrumentation |  |
|  | Implants |  |
|  | Anesthesia (Machine Checklist) |  |
|  | Case Specific Procedures |  |
|  | Supplies Available |  |
| OR Room Available and Ready | PACU Ready | Bed Available (ICU, CCU, Floor, or Day Surgery) |
|  |  | PACU Ready for Patient |
|  | Counts (Sponge/Needle) |  |
|  | Instrumentation Count/ Verification |  |
| Pre-Op Education |  |  |

As shown in FIGS. 2–4, indicators for the above events and activities are displayed on the individual screens with the status for each event and activity shown by the color and shape of each indicator. The user can quickly glance at the "Pre-Operative" screen to determine whether all activities have green indicators (and/or corresponding circular shape), indicating that the patient is ready to proceed to the operative phase. For any indicators revealing a yellow or red color (and/or corresponding triangular or octagonal shape), the user can access the status list to determine whether further actions are necessary.

Furthermore, in some embodiments it may be desirable to allow the user to move from screen to screen, to assess the status of other environments. Thus, when viewing the "Pre-Operative" screen 110 in the illustrative example, the user can use buttons 160 and 162 to page forward to the "Operative" 210 and "Post-Operative" 310 screens. From the "Operative" screen 210, the user can use button 262 to page forward to "Post-Operative" 310 or use button 258 to page backwards to "Pre-Operative" 110. Similarly, once at the "Post-Operative" screen 310, the user can use buttons 358 and 362 to page backward to the either of the first two screens. Optionally, the user can go directly to a particular screen (illustratively selected from a navigation bar) without paging. Such a feature is particularly useful for embodiments having a plurality of additional screens, wider displays, or other visual projection devices (including, but not limited, to holographic projection devices).

The systems of the present invention may optionally include one or more of the following features:
  Front end web based screens
  Data entry and radio button/toggle switch inputs
  Back end ODBC compliant database
  User friendly GUI
  Highlighted stop light display of status of events and activities
  Positional highlighting of status of events and activities
  Running status change based on altered events and activities
  Drop down sub values of each event or activity (may be a 1:1 or 1:many association)
  "Not Applicable" button to indicate the event or activity does not apply
  Individual and cumulative grading of each event and activity
  Scoring of events and activities
  Rapid performance—sufficient server and infrastructure capacity
  Security
  Support of multiple ORs
  PCs or other interface devices in each OR
  Touch Screen support on the PC as well as keyboard and mouse
  802.11b/g Wireless Hand Held support for entering data and status
  802.11b/g Access Points
  Wireless DEC and VPN Encryption
  Data and application backup and recovery
  Data feeds from Cerner, Careweb, Regenstrief, or other information systems
  ASP capability to refresh dynamic status of screens, events, and activities
  Ability to turn application "On" or to display a "Time Out" screen in which the indicator state will not be displayed depending upon experimental randomization.
  Advanced technology
    Oracle or SQL
    VBA or JAVA
    Linux, Apache, MySQL
  Central Randomization
  Central report generation
  Daily compliance feedback report by site In testing the system, training, in obtaining information regarding sentinel events, or in using the system for other scientific purposes, randomization of various alert states may be employed. For example, in one exercise, the system will display either an alert condition (such a the red stop sign) or a non-relevant image for one or more indicators, depending on whether a particular input value is odd or even. In another example, randomization may be used to support a random allocation design. In this example, based on satisfaction of one or more criteria, either an alert condition or a non-relevant image is displayed. Such predefined criteria illustratively may be one or more of the following: patient age, patient gender, patient race, surgical procedure, or surgeon. Various other criteria, as are appropriate for the particular study, may be employed in the random allocation design.

The systems herein described can also be used to understand better the events that lead to sentinel events. Feedback from the alerting system can be used to study such events and the information obtained can be used to modify the sets of status lists to reduce future sentinel events.

It will be appreciated by those of skill in the art that the systems of the present invention may be used for a variety of healthcare environments and activities for those environments beyond that illustrated herein. For example, a system of the present invention could be used in the intensive care unit, on the hospital floor, at a patient's bedside, in a nursing station, at a physician workcenter, in a physician's office, in physical therapy, in a social work setting, as well as on mobile platforms such as an ambulance, an aircraft, or helicopter. Appropriate indicators may be selected for one or more phases in each of these exemplary healthcare environments. In an illustrative example for use in many of these settings would be reminders to reacquire a manual blood pressure measurement after a period of time An indicator could become a yellow triangle after a set period of time, and then go to the red stop sign after a longer period of time, unless the appropriate blood pressure measurement is taken.

Although the invention has been described in detail with reference to preferred embodiments, variations and modifications exist within the scope and spirit of the invention as described and defined in the following claims.

The invention claimed is:

1. A patient safety alerting system comprising
an output device comprising a set of visual indicators, each visual indicator displaying one of a plurality of indicator states, each of the indicator states indicating a level of compliance with patient safety procedures,
a set of status lists, each status list corresponding to its respective visual indicator, wherein the displayed indicator state of the respective visual indicator corresponds to information in the respective status list, each status list provided for containing information regarding the status of a patient for a component or activity,
a processing unit operatively connected to the output device for processing changes to the status lists and corresponding visual indicators, and
an input device operatively connected to the processing unit and configured to interface with a user to allow the user to access information in any of the status lists.

2. The system of claim 1 wherein the set of visual indicators is provided on a single computer screen.

3. The system of claim 2 wherein the indicator state of each of the visual indicators is discernable from a distance of ten feet.

4. The system of claim 2 wherein the set of visual indicators indicate the status for a first phase of patient care.

5. The system of claim 4 further comprising a second set of visual indicators, with respective indicator states and a respective second set of status lists, wherein the second set visual indicators indicate the status for a second phase of patient care.

6. The system of claim 5 wherein the first set of visual indicators is displayed on a first screen and the second set of visual indicators is displayed on a second screen.

7. The system of claim 6 further comprising a third set of visual indicators, with respective indicator states and a respective third set of status lists, wherein the third set of visual indicators indicate the status for a third phase of patient care.

8. The system of claim 7 wherein the first phase is pre-operative care, the second phase is operative care, and the third phase is post-operative care.

9. The system of claim 1 wherein the user can use the input device to update the information.

10. The system of claim 1 wherein at least some of the information is obtained from another system that is connected to the processing unit.

11. The system of claim 1, further comprising an alarm operatively connected to the processing unit for activation when one or more indicator states indicates an unacceptable level of compliance with patient safety procedures.

12. The system of claim 1 wherein at least one displayed indicator state is selected based on randomization of a value of information in one or more of the status lists.

13. A patient safety alerting system comprising
a Pre-Operative set of status lists, an Operative set of status lists, and a Post-Operative set of status lists,
a processing unit for storing and processing information needed for each of the status lists, and
a computer monitor displaying an environment screen selected from the group consisting of a Pre-Operative screen comprising a Pre-Operative set of indicators, an Operative screen comprising a set of Operative indicators, and a Post-Operative screen comprising a set of Post-Operative visual indicators, each visual indicator corresponding to its respective status list and capable of displaying a plurality of indicator states, wherein the displayed visual indicator for each indicator state reflects information stored for its respective status list, and all visual indicators of the displayed environment screen are visible at one time, and
an input device configured to interface with a user to allow the user to view and change information in the status lists.

14. The system of claim 13 wherein the input device also allows the user to select and display one of the other environment screens.

15. The system of claim 13 wherein the visual indicator states comprise red, yellow, and green symbols.

16. The system of claim 15 wherein the red symbol is octagonal, the yellow symbol is triangular, and the green symbol is circular.

17. A method for providing for enhanced patient safety comprising
providing a plurality of sets of status lists, wherein each set of status lists comprises the components and activities for a patient in one of a plurality of hospital environments, and each of the status lists holds information for one component or activity relevant to its respective environment,
providing a processing unit for storing and processing information needed for each of the status lists and for providing information to a screen,
displaying the screen comprising a set of visual indicators for one of the environments, each visual indicator corresponding to its respective status list and capable of displaying a plurality of indicator states, wherein the displayed visual indicator for each indicator state reflects information stored for its respective status list, and all visual indicators of the displayed environment screen are visible at one time, and
viewing the screen to check the status for the patient in the environment.

18. The method of claim 17, further comprising the step of
using an input device operatively, connected to the processing unit to update information in the status lists, wherein the user can access the information in one or more particular status lists without moving sequentially through each of the status lists.

19. The method of claim 18, wherein the indicator state for one of the visual indicators changes upon expiration of a set time subsequent to updating the information in one of the status lists.

20. The method of claim 18, further comprising the step of
using the input device to change the screen to display a second set of visual indicators for another one of the environments.

21. The method of claim 17 wherein one of the visual indicator states is a stop sign.

22. The method of claim 21, further comprising the step of delaying further patient treatment if any of the indicators are displaying the stop sign.

23. The method of claim 17 wherein the processing unit is connected to another hospital system and the method further comprises the step of receiving information needed for one of the lists from the other hospital system.

24. The method of claim 17, further comprising the step of providing a quality assurance program with at least some of the information held in the status lists.

* * * * *